United States Patent [19]

Crockford et al.

[11] 4,323,546

[45] Apr. 6, 1982

[54] METHOD AND COMPOSITION FOR CANCER DETECTION IN HUMANS

[75] Inventors: David R. Crockford, Haverhill, Mass.; Buck A. Rhodes, Albuquerque, N. Mex.

[73] Assignees: Nuc Med Inc., Albuquerque, N. Mex.; University Patents Inc, Norwalk, Conn.

[21] Appl. No.: 37,992

[22] Filed: May 14, 1979

Related U.S. Application Data

[63] Continuation-in-part of Ser. No. 908,568, May 22, 1978, abandoned.

[51] Int. Cl.³ ............... A61K 49/00; A61K 43/00; G01T 1/00; B65D 71/00
[52] U.S. Cl. ............... 424/1; 260/112 B; 128/659; 424/1.5; 424/9; 422/61
[58] Field of Search ............... 424/1, 9, 1.5; 260/112 B; 128/659; 422/61

[56] References Cited

U.S. PATENT DOCUMENTS

3,927,193 12/1975 Hansen et al. ............... 424/1
4,150,149 4/1979 Wolfsen et al. ............... 424/1

OTHER PUBLICATIONS

McManus et al., Can. Res., 36, pp. 2367-3481, Sep. 1976.

*Primary Examiner*—Edward A. Miller
*Assistant Examiner*—Christine M. Nucker
*Attorney, Agent, or Firm*—Paul J. Cook

[57] ABSTRACT

Anti human chorionic gonadotropin (anti-hCG) and/or anti human chorionic gonadotropin- beta subunit (anti-hCG-β) labeled with Technetium-99M are/is administered to a human. The biodistribution of the labeled composition is monitored in order to determine whether the labeled composition accumulates at cancer sites, e.g. tumors that produce human chorionic gonadotropin (hCG), human chorionic gonadotropin-like material, and a compound similar to and/or identical to the beta-chain of chorionic gonadotropin, or mixtures thereof which would bind specifically to anti-hCG and/or anti-hCG-β.

12 Claims, 3 Drawing Figures

METHOD AND COMPOSITION FOR CANCER DETECTION IN HUMANS

REFERENCE TO RELATED APPLICATION

This application is a continuation-in-part of Ser. No. 908,568, filed May 22, 1978, abandoned.

BACKGROUND OF THE INVENTION

This invention relates to compositions and methods capable of detecting cancer cells or malignant tumors in humans. More particularly, this invention relates to compositions radio-labeled with Technetium-99m which, when administered to a human will accumulate at cells producing hCG, hCG-like material, and a compound similar to and/or identical to the beta-chain of chorionic gonadotropin, or mixtures thereof.

The use of compositions which emit radiation at levels which can be detected after administration to the human body are well known. These compositions are utilized to visualize and/or monitor functioning of various parts of the body or are utilized diagnostically to determine the presence or absence of particular antigens, antibodies, hormones or the like. In one particular aspect of the prior art, radiolabeled antibodies are utilized to detect tumors having associated therewith carcinoembryonic antigen. As disclosed in U.S. Pat. Nos. 3,663,684, 3,867,363 and 3,927,193, $I^{131}$ or $I^{125}$ labeled antibodies to carcinoembryonic antigen are utilized to detect tumors which produce or are associated with carcinoembryonic antigen. It is also well known that protein molecules can be tagged with Technetium-99m in order to form diagnostic agents. It has also been proposed to tag the antibody of the beta chain of human chorionic gonadotropin with peroxidase (McManus et al, Cancer Research, 36, pp. 2367-3481, September, 1976) in order to localize the antigen in malignant tumors.

Recently, it has been found that neoplastic tissues produce chorionic gonadotropin, chorionic gonadotropin-like material, and a compound similar to and/or identical to the $\beta$-chain of chorionic gonadotropin (hCG-$\beta$ subunit) or mixtures thereof, specifically to the degree where it is considered more cancer specific than either carcinoembryonic antigen (CEA) or alphafetoprotein (AFP). The positive identification of chorionic gonadotropin in a heterogenous group of cancer cells and its absence in non-cancer cells in tissue culture has suggested that:

(a) this is a unique trophoblastic-like sialoglycoprotein which is synthesized de-novo by the malignant cells;

(b) since CG and/or CG-like glycoprotein has been observed only in the trophoblast and human spermatozoa, its production by the cancer cells can only be explained by an expression of the information which opens the mechanism(s) for its biosynthesis, either by derepression or by an activation of the genetic control;

(c) the compound is a common antigen (common denominator) of every cell with oncogenic properties. It is also believed that chorionic gonadotropin is one of the factors involved in maternal immunosuppression. In support of this belief, it has been shown that chorionic gonadotropin has been shown to block maternal lymphocyte cytotoxicity, maternal lymphocyte mitosis and to inhibit phytohemagglutin-induced and mixed lymphocyte blast transformation.

While peroxidase-labeled or fluorescein-labeled anti-hCG-beta or anti-hCG are effective for identifying and localizing malignant cells, these labeled compositions are undesirable for in-vivo use because they do not allow for visualization by any available detection system and are otherwise undesirable for widespread use because they are simply an invitro immunohistochemical technique requiring light or electron microscopy of biopsy samples for positive identification.

Accordingly, it would be highly desirable to provide a labeled anti-hCG-beta or anti-hCG which can be utilized invivo and which overcomes the disadvantages of the prior art compositions.

SUMMARY OF THE INVENTION

In accordance with this invention, radiolabeled compositions are provided which comprise anti-hCG-beta or anti-hCG labeled with Technetium-99m. These compositions are administered parenterally to humans and the biodistribution of the labeled composition is monitored by scintigraphy in order to locate cancer cells or malignant tumors. The present invention provides substantial advantages over the prior art since the compositions utilized are more specific toward cancer cells or malignant tumors than the compositions of the prior art, the technique can be performed in-vivo, the compositions are safer to use and are more effective than compositions labeled with $I^{125}$ or $I^{131}$, and $I^{123}$. A kit also is provided which includes anti-hCG-$\beta$ and/or anti-hCG, as well as a suitable reducing agent capable of reducing Tc-99m from Tc (VII) to Tc (IV), which is added by the user prior to administration to humans. The kit also may contain a chromatographic column containing a material capable of binding Technetium as the pertechnetate, or as a complex of Technetium as well as being capable of binding a reducing agent which reduces Technetium (VII) to Technetium (IV).

DESCRIPTION OF SPECIFIC EMBODIMENTS

Figure 1:
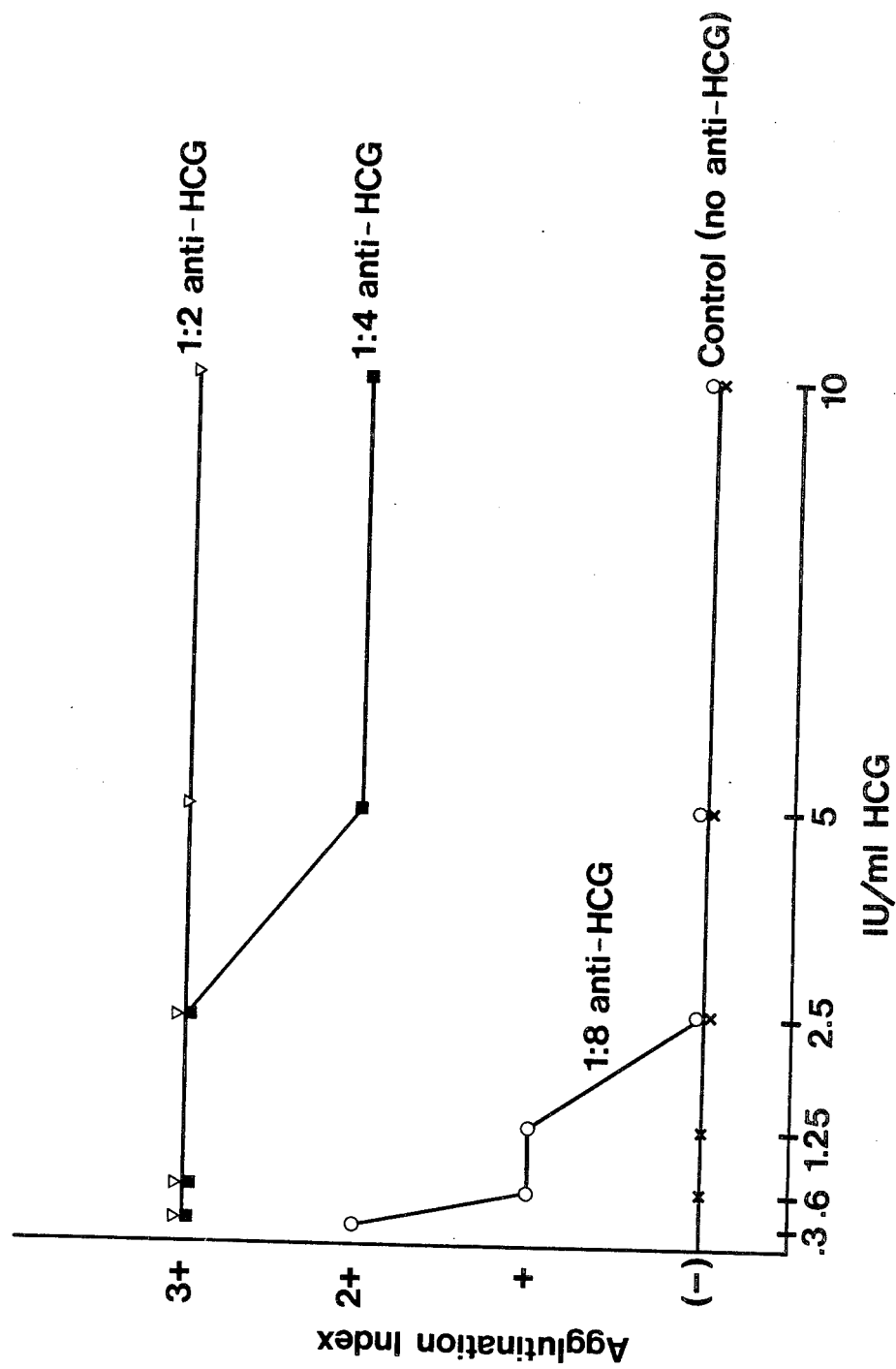
FIG. 1 shows that anti-hCG effects significant agglutination of cancer cells.

Human chorionic gonadotropin (hCG) is a molecule believed to have a molecular weight ranging from about 35,000 and 38,000. HCG is found in the urine and sera of pregnant women, in patients with trophoblastic tumors and in the normal placentas and is produced by certain cell cultures. HCG consists of two noncovalently bonded alpha and beta chains having approximate molecular weights of 14,700 and 23,000 respectively. The alpha and beta chains can be easily dissociated; however, it has been shown that each chain is biologically inactive as a separate entity. The amino acid sequence of the alpha chain has been shown to have close similarity to the alpha chain of luteinizing follicle stimulating hormone and thyroid stimulating hormone. The beta chain has similarity only to the beta chains of luteinizing hormone and less homology to those of follicle stimulating hormone and thyroid stimulating hormone. The beta chain is immunologically active in both the intact hormone and as a separate entity. Approximately 30 percent of the molecule is carbohydrate which is constituted by six different monosaccharides: sialic acid, L- fructose, D-galactose, D-mannose, N-acetylglucosamine and N-acetylgalactosamine.

The source of the Technetium-99m preferably is water soluble such as the alkali or alkaline earth metal pertechnetate. The Technetium can be obtained as Sodium pertechnetate Tc-99m from a conventional 99Mo/99mTc generator. Any source of pharmaceutically acceptable Technetium-99m may be utilized in the present invention.

Anti-hCG or anti-hCG-$\beta$ serum is obtained by any conventional method such as by immunizing animals such as rabbits, sheep, goats, or other suitable species with hCG or hCG-$\beta$ in order to induce production of the hCG antibody or hCG-$\beta$ antibody. Serum then is harvested from the immunized animals and the specific anti-hCG or anti-hCG-$\beta$ immunoglobulins then can be obtained in sufficiently pure form such as by affinity chromatography, immunoprecipitation, non-immune precipitation or the like. In affinity chromatography, for example, an hCG rich fraction first is isolated such as from pregnant female serum or urine by conventional nonimmune precipitation or immunoprecipitation techniques followed by chromatography on DEAE-cellulose followed by gel filtration on Sephadex G-100 or by another suitable purification technique. The hCG-rich fraction thus obtained is passed onto a column of a cyanogen halide activated or periodate activated gel such as Sephadex, Sepharose, or cellulose or another insoluble polysaccharide with carboxyl, polyhydroxyl or N-hydroxylsuccinimide ester functionality in order to chemically attach the hCG by a weak covalent bond to the gel. The serum obtained from the animal then is passed through the column and the anti-hCG or anti hCG-$\beta$ becomes specifically attached to the hCG, its corresponding antigen, in the column while the remainder of the other immunoglobulins and non-specific antigens pass through the column. The anti-hCG or anti-hCG-$\beta$ then is recovered from the column by passing an appropriate buffer, e.g. acetate or phosphate solution through the column in order to break the weak covalent bond between the anti-hCG or anti-hCG-$\beta$ and the hCG-gel matrix.

The anti-hCG beta or anti-hCG can be obtained in any conventional manner such as by elution with solution or buffer of appropriate ionic strength and pH.

The Technetium-99m labeled anti-hCG or anti-hCG-beta is prepared by acidic, basic or neutral (ligand-exchange) radio-labeling techniques. In one particular and preferred aspect of this invention, the labeled anti-hCG or anti-hCG-beta is obtained by a ligand exchange process. In this process, a solution of Technetium (IV) is prepared by mixing a solution of Technetium such as in the form of a pertechnetate ($TcO_4^-$) and saline with a stannous reducing solution, e.g. stannous fluoride-acetate having a pH between about 3 and 5.5. In this procedure, the stannous ions reduce Technetium (VII) to Technetium (IV). The reduced Technetium-99m first is chelated onto the top of a column of Sephadex G-25 (dextran cross-linked with carboxyl functionality) by passing the aqueous solution of Technetium-99m through the column. The solution has a pH between about 5.5 and 7.0. The column then is washed with saline to essentially remove free Pertechnetate ($TcO_4^-$) or unusual species of Technetium thereby leaving the Technetium-99m chelated or adsorbed or otherwise bound to the column. A physiologic solution of anti-hCG and/or anti-hCG-beta then is prepared with appropriate buffer so that the resultant solution has a pH between about 6 and 9, preferably between about 7 and 8. When operating within this pH range, denaturation of anti-hCG or anti-hCG-beta is eliminated or minimized. The protein is then added in a minimum volume to the top of the column where the Technetium-99m/Stannous complex is bound and where it is allowed to stand until the Technetium-99m is bound to the protein having stronger bonding sites than the column material. This usually occurs within about 30 minutes. The column then is washed to remove the labeled anti-hCG or anti-hCG-$\beta$. Washing can be effected with a known volume of human serum albumin diluted with 50/50 ACD or the like followed by a known volume of saline. In this matter, the volume of washing saline solution containing the labeled protein can be determined and the labeled protein can be collected. Impurities in the anti-hCG or anti-hCG-beta will remain on the column or will be eluted at a rate different from that of the labeled, immunologically intact, anti-hCG or anti-hCG-.

A second preferred method for forming Technetium-99m labeled anti-hCG or anti-hCG-beta comprises direct labeling of the protein. In this method, a buffered solution is admixed with an acidic solution of $SnCl_2$ which is a reducing agent for pertechnetate. The buffered solution can comprise sodium and or potassium phthalate, tartrate, gentisate, acetate, borate or mixtures thereof having a pH of between 4.5 and 8.0, preferably about 5.5. Tartrate is utilized to maintain the appropriate concentration of stannous ion in solution to effect the desired solution pH. The $SnCl_2$ preferably is added to the buffer as a solution with concentrated HCl. Thereafter, the solution is neutralized such as with sodium hydroxide to attain a pH of between about 4.5 and 8.0, preferably about 5.5. The anti-hCG and/or anti-hCG-beta then is added to the neutralized solution in an amount to attain a concentration of protein up to just less than that which would begin to precipitate the protein in the buffer being used. In order to attain the desired degree of protein labeling, the resultant stannous ion, buffer, protein solution is allowed to incubate. For example at room temperature, the incubation time should be at least about 15 hours, preferably at least about 20 hours. If desired, this solution can be heated moderately to reduce the incubation time. The solution then can be either freeze-dried and subsequently reconstituted for admixture with pertechnetate or can be admixed directly with pertechnetate solution to obtain the labeled protein. If desired, the resultant radiolabeled protein may be further purified to separate the labeled protein from free technetium such as by chromatography in a Sephadex column. However, this last step is unnecessary.

The present invention also provides a kit with which a user can prepare the composition of this invention and administer it to a patient relatively quickly after preparation. The kit includes anti-hCG and/or anti-hCG-beta either in lyophilized form, frozen, or liquid of suitable ionic strength and pH, and either containing or not containing a reducing agent. If without the reducing agent, the anti-hCG or anti-hCG-beta can be admixed with a reducing solution or solid provided within the kit and in a separate container. Representative, suitable reducing agents are $SnCl_2$ or $SnF_2$ to be dissolved or already dissolved in an appropriate solution, such as sodium acetate/acetic acid, acidified deionized or distilled water, or the like, such that a reducing pH of about 3 to 5.5 is obtained when combined with Technetium-99m as Sodium pertechnetate. Therefore, Technetium-99m as pertechnetate is either reduced in the presence of reducing agent prior to addition to the anti-hCG or anti-hCG-β or is reduced when added to the anti-hCG or anti-hCG-β containing reducing agent. The solution of labeled anti-hCG and/or anti-hCG-beta is then suitable for administration to a patient.

In an alternative embodiment of this invention, the kit can include a container for a column of material which entraps or otherwise binds Technetium-99m such as Sephadex, Sepharose or cellulose. The column of this material also can contain the reducing agent for Technetium or the reducing agent can be added thereto when it is desired to reduce the Technetium.

In forming the products of this invention, a solution of the Technetium-99m as the pertechnetate is poured onto the column in order to bind the Technetium thereon. A physiologically acceptable aqueous solution of the anti-hCG or anti-hCG-beta then is poured onto the column in order to bind the labeled Technetium to the anti-hCG or anti-hCG-beta. The labeled protein then is eluted from the column with saline or an otherwise appropriate buffer and is collected from the bottom of the column in a form suitable for intravenous administration to a patient. In an alternative embodiment, the eluted labeled protein is passed through a bed of anion exchange resin in order to remove free pertechnetate from the labeled protein thereby to form a pure labeled anti-hCG or anti-hCG-beta or mixtures thereof, substantially free of radiochemical contamination. If desired, these anion exchange resins need not be part of the columns utilized for labeling but can comprise a separate bed through which the labeled protein is passed.

The labeled anti-hCG or anti-hCG-beta is administered by intravenous injection in a pharmaceutically acceptable saline solution, sterile and pyrogen-free. Suitable dosages are usually between about 5 and 30 millicuries, preferably between about 10 and 20 millicuries of Technetium-99m anti-hCG and/or Technetium-99m anti-hCG-beta for the normal 70 kg patient. The patient then can be scanned by conventional scintigraphy within about 1 hour to about 6 hours after administration of the labeled protein. Tumors are located in those areas showing a high concentration of labeled anti-hCG and/or anti-hCG-beta.

The following example illustrates the present invention and is not intended to limit the same.

EXAMPLE I

This example illustrates a ligand exchange process for obtaining the anti-hCG-beta or anti-hCG of the present invention. Anti-hCG or anti-hCG-beta is obtained from Serono Laboratories, Inc. Technetium-99m is obtained from New England Nuclear Corporation. To 0.1 to 5.0 ml of an aqueous solution of Sodium Pertechnetate Tc-99m (pH 5 to 7) is added 0.1 ml of an aqueous acetate solution containing stannous fluoride, pH 3 to 5.5. The stannous ions reduce the pertechnetate ions to Technetium IV. The solution then is poured into a sterile 5 cc column of Sephadex G-25 and then reduced Technetium is bound to the very top of the column. The column then is washed with saline (NaCl) solution to remove any free pertechnetate and other unbound species of Technetium. A solution of proper ionic strength and pH containing anti-hCG-beta or anti-hCG is added to the top of the column. After about 30 minutes, substantially complete ligand exchange occurs to bind the Technetium to anti-hCG or anti-hCG-beta. The column then is washed with 1 cc of human serum albumin diluted 50/50 with ACD (Acidified-Citrate-Dextrose). After the albumin solution has soaked completely into the column, 5 cc of saline is added to the column, and the sixth cc of eluate is collected which contains the Technetium-99m anti-hCG-beta or anti-hCG.

EXAMPLE II

This example illustrates a direct method of labeling to form the anti-hCG beta or anti-hCG of this invention. Anti-hCG or anti-hCG-beta is obtained from Serono Laboratories, Inc., Technetium 99m is obtained from New England Nuclear Corporation.

To 0.4 ml of a 50 mM of sodium-potassium tartrate buffer (pH 5.50) (10.51 g/l, pH adjusted to 5.50 with 50 mM tartaric acid) is added 1.6 ml of a 50 mM potassium biphthalate buffer (pH 5.50) (10.21 g/l, pH adjusted to 5.50 with 10 N NaOH). To the resultant buffer solution is added 0.02 ml of 0.5 M $SnCl_2$-HCl (94.8 g/l conc. HCl). The resultant solution is tartrated back to a pH of $5.65\pm0.05$ by adding thereto 0.02 ml of 10 N NaOH and the resultant solution is adjusted to a pH of $5.65\pm0.05$ with with 1 N NaOH. To this solution is added 0.3 ml of a saline solution of anti-hCG or anti-hCG-beta (10 mg protein/ml saline). The reaction vessel is allowed to stand approximately 21 hours at room temperature. Thereafter, 0.2 ml of $NaTcO_4$ with an activity of about 20 $\mu$Ci is added to protein-containing composition and allowed to stand about 1 hour to effect substantially complete labeling of the protein prior to use, the resultant product is passed through a Sephadex column to remove free technetium from the labeled protein product.

EXAMPLE III

This example illustrates that technetium labeled anti-hCG is stable in the presence of a tin reducing agent and/or in the presence of a buffer needed to maintain reducing conditions for technetium. In addition, this example illustrates that cancer cells include hCG on the outer membrane surface and that hCG on the surface of cancer cells can be coupled with labeled anti-hCG; thereby in effect identification of cancer cells.

Figure 2:
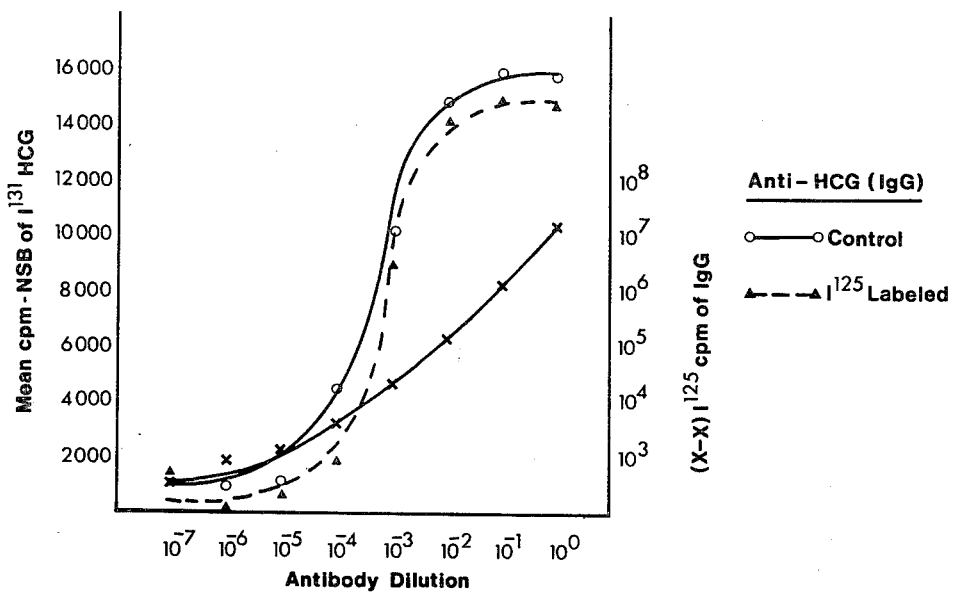
FIG. 2 shows the effect of agglutination of iodine-125 and iodine-131.

In order to determine whether technetium 99m labeled anti-hCG is stable in the presence of tin and/or a buffer solution required to maintain reducing conditions, hCG was subject to serial dilution testing. In a preliminary screening test, $I^{131}$ labeled hCG was admixed with serial dilutions an IgG fraction of either anti-hCG or $I^{125}$ labeled anti-hCG and the resultant product was precipitated with 60% $(NH_4)_2SO_4$ following an 18 hour incubation and in each case was tested to determine the concentration of radioactive iodine with a gamma counter. As shown in FIG. 2, the effect of labeling with radioactive $I^{125}$ had little effect on the degree of precipitation over a serial dilution range of 1:1 ($10^\circ$) to $1:10^7$ ($10^{-7}$). This is shown by the fact that the dilution curves with anti-hCG and $I^{125}$ labeled anti-hCG are substantially parallel and only slightly offset from each other.

In each case, the $I^{131}$ labeled hCG or $I^{125}$ anti-hCG was prepared as follows: To 100 $\mu$l of 0.01 m sodium phosphate buffer at a pH of 7.5 was added 25 $\mu$l of hCG (or anti-hCG) in saline (40 mg/ml, 1 mg). To the resultant solution was added 5 $\mu$l of sodium iodide ($I^{125}$ or $I^{131}$). Thereafter 50 $\mu$l (1 mg/ml) of chloramine T in 0.01 M phosphate buffer was added in order to initiate iodination. The resultant solution was incubated at room temperature for about four minutes and thereafter is mixed with 50 ml. of 2.4 mg/ml sodium metabisulfite in 0.01 M sodium phosphate buffer in order to stop the reaction. This solution then was incubated at room temperature for about two minutes. Thereafter 0.3 ml of 1% bovine serum albumin (BSA) in 0.01 M sodium phosphate buffer was added in order to serve as a carrier protein. The composition then is passed through a 1×8-200 Dowex column prewashed with 1% BSA to separated free iodine from the composition. The iodinated sample recovered from the column was used as described above.

Figure 3:
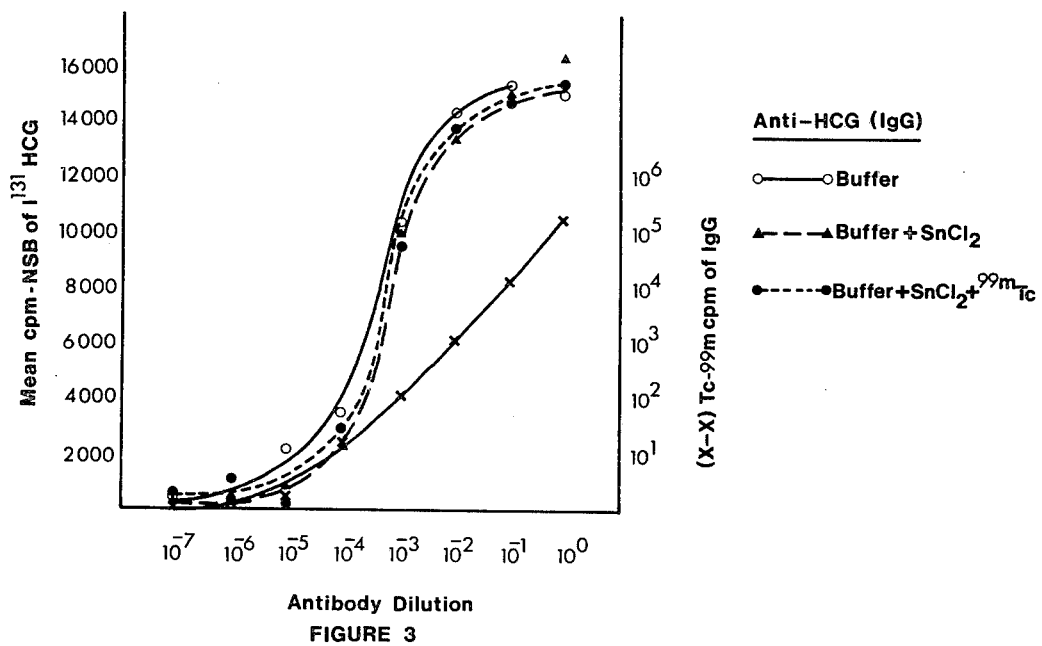
FIG. 3 shows the effect of agglutination of iodine-131 and technetium-99m.

Subsequent to the screening test set forth above, hCG labeled with $I^{131}$ was tested with serial dilutions of compositions comprising (a) anti-hCG and a buffer composition comprising 80% (volume/volume) 50 mM phthalate and 20% 50 mM tartrate at pH 5.5; (b) anti-hCG, the buffer composition and $SnCl_2$; and (c) $Tc^{99m}$ labeled anti-hCG prepared in the manner set forth in Example II, the buffer composition and the $SnCl_2$. The serial dilution ranged from 1:1 ($10^0$) to $1:10^7$ ($10^{-7}$). In each case the precipitated product was monitored for radioactive $I^{131}$ and/or $Tc^{99m}$ with a gamma counter. As shown in FIG. 3, compositions a, b, and c resulted in little or no effect on protein stability since the dilution curves for each are essentially parallel and offset to only a small degree if any.

In a second test to determine whether anti-hCG effects agglutination of cancer cells, a balanced salt solution suspension of K562 human leukemia cells (obtained from UNM Cancer Center) was mixed with serial dilutions (1:2 to 1:8) of anti-hCG in saline to determine the resultant degree of agglutination. The degree of agglutination was measured by an agglutination index wherein 3(+) means high, 2(+) means moderate, (+) means slight and (−) means no agglutination. As shown in FIG. 1, wherein agglutination index is plotted against International Units (IU) per ml of hCG, anti-hCG indeed effects significant agglutination of the cells. The agglutination was inhibited by the addition of hCG in a dose dependent manner, which shows that the cell surface has hCG hereon.

In a third test, fluorescein isothiocyanate labeled rabbit antibody to sheep IgG wa utilized to determine photographically whether cancer cells express hCG on their surface. Four different samples of cancer cells in balanced salt solution were utilized in the tests. They were Tera II and JEG (obtained from Sloan Kettering Memorial Cancer Institute) Chang liver and BeWo (obtained from American Type Culture Collection). In each case, the cell suspension was admixed with sheep antibody to hCG under the following conditions: Cells were reacted with 1:20 diluted IgG fraction of anti-hCG for 30 minutes at 37° C., followed by two washes in a balanced salt solution. Thereafter, the fluorescein isothiocyanate labeled antibody was mixed with the cell suspension under the following conditions: Fitc-labelled rabbit anti sheep IgG versus obtained from Miles Research Laboratories (Elkhart, Indiana) and was reacted with the cells at a dilution of 1:15 for 30 minutes at 37° C. Cells were then washed two times in a balanced salt solution. The resultant cell product then was photographed under ultraviolet light at 160× magnification.

We claim:

1. A composition of matter selected from the group consisting of Technetium-99m labeled anti-human chorionic gonadotropin, Technetium-99m labeled anti-human chorionic gonadotropin-beta and/or mixtures thereof.

2. The composition comprising Technetium-99m labeled anti-human chorionic gonadotropin.

3. The composition comprising Technetium-99m labeled humna corionic gonadotropin beta.

4. A diagnostic kit suitable for forming a composition useful in identifying a cancer cell and/or a malignant tumor which comprise a sterile package containing a protein comprising anti-human chorionic gonadotropin, anti-human chorionic gonadotropin beta or mixtures thereof, and means for mixing the contents of said sterile package with reduced Tc-99m in a physiologically acceptable aqueous solution.

5. The kit of claim 4 wherein a physiologically acceptable reducing agent useful in reducing Technetium (VII) to the Technetium (IV) state is admixed with said protein.

6. The kit of claim 4 wherein said protein in said sterile package is lyophilized.

7. The kit of claim 4 wherein said protein and reducing agent are lyophilized.

8. The kit of claim 4 which includes a column of material capable of binding technetium in the IV state and of releasing said technetium when contacted with a solution of anti-human chorionic gonadotropin, anti-human chorionic gonadotropin-beta or mixtures thereof.

9. The kit of claim 4 which includes an anionic exchange resin capable of selectively removing pertechnetate ion from a solution containing pertechnetate ion from a protein labeled with Technetium-99m.

10. The method of detecting cancer cells and/or a malignant tumor in a human which comprises injecting the composition of claim 1 into the human and scanning the human by scintigraphy, a means for detecting gamma radiation from said composition within the body of said human.

11. The method of detecting cancer cells and/or a malignant tumor in a human which comprises injecting the composition of claim 2 into the human and scanning the human by scintigraphy, a means for detecting gamma radiation from said composition within the body of said human.

12. The method of detecting cancer cells and/or a malignant tumor in a human which comprises injecting the composition of claim 3 into the human and scanning the human by scintigraphy, a means for detecting gamma radiation from said composition within the body of said human.

* * * * *